United States Patent
Tan et al.

(10) Patent No.: US 7,495,028 B2
(45) Date of Patent: Feb. 24, 2009

(54) R-BAMBUTEROL, ITS PREPARATION AND THERAPEUTIC USES

(76) Inventors: Wen Tan, c/o Steve Tan, 18223 Swiss Cir., Unit 2, Germantown, MD (US) 20874; Jiang Long Cheng, c/o GLSynthesis Inc., One Innovation Dr., Worcester, MA (US) 01605

( * ) Notice: Subject to any disclaimer, the term of this patent is extended or adjusted under 35 U.S.C. 154(b) by 241 days.

(21) Appl. No.: 11/053,014

(22) Filed: Feb. 8, 2005

(65) Prior Publication Data
US 2005/0171197 A1    Aug. 4, 2005

Related U.S. Application Data

(63) Continuation of application No. PCT/US02/25225, filed on Aug. 8, 2002.

(51) Int. Cl.
*A61K 31/27* (2006.01)
*C07C 261/00* (2006.01)
(52) U.S. Cl. ..................... 514/483; 560/132
(58) Field of Classification Search ............ 514/483; 560/132
See application file for complete search history.

(56) References Cited

U.S. PATENT DOCUMENTS 4,419,364 A * 12/1983 Olsson et al. ............... 514/479

FOREIGN PATENT DOCUMENTS

GB        2 255 503       11/1992
WO       WO 91/13615      9/1991

OTHER PUBLICATIONS

Lipid Metabolism:hereditrary disorders : Merck Manual Home edition, Feb. 1, 2003. p. 1-4.*
Aldrich, 1998-1999, p. 688, a copy of two pages.*
International Search Report issued in International Application No. PCT/US02/025225 mailed Jul. 2, 2004, 1 page.
European Search Report issued in European Patent Application No. 02807678.4-2017 (PCT/US0225225), dated May 8, 2006, Cheng, J. L., et al. (3 pages).
Carlsson, Y., et al.: "Non-aqueous capillary electrophoretic separation of enantiomeric amines with (-)-2, 3:4, 6-di-0-isopropylident-2-keto-L-gulonic acid as chiral counter ion", Journal of Chromatography, A, 922 (1-2), 303-311, CODEN: JCRAEY; ISSN: 0021-9673, 2001, XP004255350 (9 pages).

* cited by examiner

*Primary Examiner*—Taylor Victor Oh

(57) ABSTRACT

R-enantiomer of Bambuterol, its preparation and therapeutic uses are disclosed. A composition includes R-Bambuterol or its therapeutically acceptable salt. A composition of R-Bambuterol includes at least 80% by weight of the R-enantiomer and not more than 20% by weight of the S-enantiomer based on a total weight of the Bmbuterol. A process includes: (a) asymmetrically reducing a suitably substituted and suitably protected bromoacetophenone compound to a chiral phenylbromoethanol comprising a primary bromo group and a secondary hydroxyl group; (b) displacing the bromo group by a suitably substituted and optionally protected primary amine to produce a protected chiral phenylethanolamine, and (c) removing the protecting groups to convert the protected chiral phenylethanolamine to a chiral phenylethanolamine.

6 Claims, No Drawings

R-BAMBUTEROL, ITS PREPARATION AND THERAPEUTIC USES

FIELD OF THE INVENTION

The present invention relates to a novel compound having therapeutic activity, to processes for its preparation, to chemical intermediates in its preparation, to pharmaceutical preparations containing it, and to the medicinal uses of the compound. The compound of the invention has potent and long lasting bronchospasmolytic effect and is effective in the treatment of bronchospasm in asthma and related conditions. The compound of the invention has potent lipid-lowering effects in treatment of hyperlipidemia, particularly in hypertriglyceridemia.

BACKGROUND OF THE INVENTION

It is desirable to find new bronchodilating agents, which have more potent activity and less side effects than the drugs which are available on the market. The compounds of the general structural formula

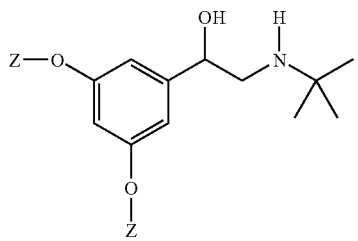

are examples of presently preferred long acting bronchodilator drugs on the market. The bronchodilator terbutaline (Z=H) is one such drug. Bambuterol (Z=C(O)NMe$_2$), the bis-dimethylcarbamate prodrug of terbutaline, has more potent bronchospasmolytic activity than the latter upon oral administration and exhibits a duration of activity of more than 12 hours. Bambuterol also exhibits a lower degree of undesired cardiovascular side effects. In addition, Bambuterol has lipid lowering effects in certain patients. (Bauer CA and Svensson LA, EP 0521967, 1990).

It is known that among many drugs having chiral centers, one enantiomer of a racemic pair is often more active than the other in treating a medical condition. For example, the levorotatory R-enantiomer of albuterol is approximately 80 times more potent as a β-2 receptor agonist than the dextrorotatory S-enantiomer (Hartley and Middlemis, J. Med. Chem., 14, 895-896, 1971), and the administration of the pure R-enantiomer offers improved therapeutic activity and fewer side effects. The United States Food and Drug Administration has approved R-albuterol hydrochloride as a new drug for the treatment of asthma. Similar results in vivo were obtained with enantiomer of terbutaline.(Kallstrom et al., Chorality 1996,8,567).

The prodrug of terbutaline, bambuterol, has a chiral center, and it can exist as a racemic mixture or as pure enantiomeric forms (Torsten et al,. U.S. Pat. No. 4,419,364, 1983). To our knowledge, no method to resolve racemic bambuterol has been discovered or published, nor has a single enantiomer of bambuterol been prepared. Thus, the biological properties and therapeutic role of either R or S bambuterol have not been studied. Racemic bambuterol has been marketed and widely used clinically for several years. It is known that the S-isomers of β-2 agonists—including terbutaline—are more toxic or less potent than the R-isomers, properties which may be responsible for the side effects of racemic bambuterol in its clinical use. The present invention teaches the preparation of single enantiomers of bambuterol of high purity, and the superior therapeutic benefits of the single R-enantiomer of the drug over racemic bambuterol.

At least two synthetic approaches have been employed to control the stereochemistry of the chiral center of albuterol and related 2-phenylethanolamines. One approach utilized in the preparation of the enantiomerically pure R and S forms of albuterol is resolution of a racemic mixture of an intermediate in its synthesis or of the final compound itself (for review see Bakale et al., Clinical Reviews in Allergy and Immunology, Vol. 14, pp 7-35, 1996). The second approach involves asymmetric synthesis, which is the de novo synthesis of a chiral substance from chiral precursors.

SUMMARY OF THE INVENTION

The present invention provides a new optically pure compound, the R enantiomer of bambuterol, and its salts as bronchospasmolytic agents. The compound is about twice as potent as racemic bambuterol in treatment of asthma, but has less inotropic and chronotropic effects. The compound of the invention also has lipid-lowering activities; it can lower plasma lipids, particularly triglycerides, in hyperlipidemic conditions. The invention also relates to methods for preparation of the pure enantiomers of bambuterol and related 2-phenylethanolamines.

The invention claims the R enantiomer of bambuterol of the following structure:

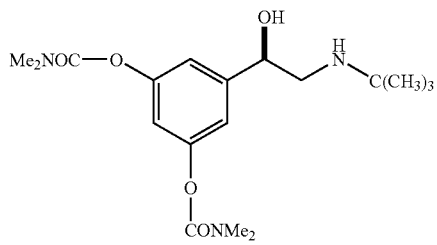

and therapeutically acceptable salts thereof The compound of the invention is of use as a bronchodilator in asthma and as a lipid-lowering drug in hyperlipidemias.

This invention also claims efficient and cost-effective synthetic methods for obtaining optically pure R-bambuterol and 2-phenylethanolamines and their synthetic intermediates, by resolution of racemic bambuterol and 2-phenylethanolamines via diastereomeric salts formation with a chiral acid, and by use of an enantioselective chemical reaction. The enantioselective synthetic method comprises the steps of:
  (a) asymmetrically reducing a suitably substituted and suitably protected α-bromoacetophenone to a chiral 2-bromo-1-phenylethanol; and
  (b) displacing the bromo group by a suitably substituted and optionally protected primary amine to produce a chiral 2-phenylethanolamine.

All objects, features and advantages are of the present invention will be further detailed in the description that follows.

DETAILED DESCRIPTION OF THE INVENTION

The invention relates to the R enantiomer of bambuterol, a compound of the following structure:

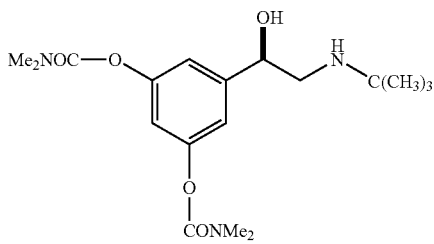

and therapeutically acceptable salts thereof

The term "pure enantiomer" means a compound of the invention comprising at least 80% by weight of one of the two chiral forms and not more than 20% by weight of the other chiral form of the compound, or more preferably 98% by weight of one of the two chiral forms and not more than 2% by weight of the other chiral form of the compound, or even more preferably 99% by weight of one of the two chiral forms and not more than 1% by weight of the other chiral form of the compound.

The methods provided by the present invention relate generally to two processes for producing a single enantiomer of a 2-phenyl-2-ethanolamine, which is obtained by Method 1: producing a racemic 2-phenyl-2-ethanolamine, resolving the racemic amine by a chiral acid, said chiral acid being selected from the group consisting of (L) and (D) tartaric acid, di-benzoyl-(L) and (I) tartaric acid, di-toluoyl-(L) and (D) tartaric acid.

Method 2: producing a suitably substituted 2-phenyl-2-ethanol bromide, a precursor to the 2-phenyl-2-ethanolamine, in high enantiomeric excess. The general steps of the methods are:

(a) asymmetrically reducing a suitably substituted and suitably protected α-bromoacetophenone to a chiral 2-bromoethanol comprising a primary bromo group and a secondary hydroxyl group;

(b) displacing the bromo by a suitably substituted and optionally protected primary amine to produce a chiral 2-phenyl-2-ethanolamine.

For the purposes of this invention, the term "suitable substituents" and equivalent terms mean substituents that when present, give rise to useful end products and intermediates thereof. In the case of chiral 2-phenyl-2-ethanolamines, preferred useful end products are P-adrenergic receptor agonists of the 2-phenyl-2-ethanolamine class including, among others, albuterol, formoterol, salmeterol, terbutaline, and bambuterol. Preferred useful intermediates of such compounds include the corresponding protected chiral 2-phenyl-2-ethanol bromide.

The term "suitable protecting group" means a group that protects an otherwise vulnerable chemical moiety of a particular compound in a specific reaction or reactions, and that can later be removed under conditions that do not destroy other functionalities that are present in the compound. Preferred suitable protecting groups for hydroxyl functionalities include ester, carbonate, carbamate, ketal, and related groups. Preferred suitable protecting groups for amine functionalities include amide, carbamate and related groups. A large number of suitable protecting groups and corresponding chemical cleavage reactions are described in "Protective Groups in Organic Chemistry", Theodore W. Greene (John Wiley & Sons, Inc., New York, 1991, ISBN 0-471-62301-6) ("Greene"). See also Kociensid, Philip J.; "Protecting Groups" (Georg Thieme Verlag Stuttgart, New York, 1994), which is incorporated by reference in its entirety herein. In particular Chapter 1, Protecting Groups: An Overview, pages 1-20, Chapter 2, Hydroxyl Protecting Groups, pages 21-94, Chapter 3, Diol Protecting Groups, pages 95-117, Chapter 4, Carboxyl Protecting Groups, pages 118-154, Chapter 5, Carbonyl Protecting Groups, pages 155-184.

The term "suitable leaving group" means a group that can be readily displaced from a reaction intermediate to produce a desired product without disturbing other functionalities present in the compound. Preferred suitable leaving groups for hydroxyl functionalities include tosylate, mesylate, trifluoroacetate and related groups. Bromine, chlorine and iodine are commonly used as leaving groups in organic synthesis.

In a preferred embodiment, the suitably substituted 2-phenyl-2-ethanol bromide is first obtained from its corresponding α-bromoacetophenone by methods well known to practitioners of the art, then the remaining steps of the process are performed. An example of this preferred embodiment is shown in Scheme 1.

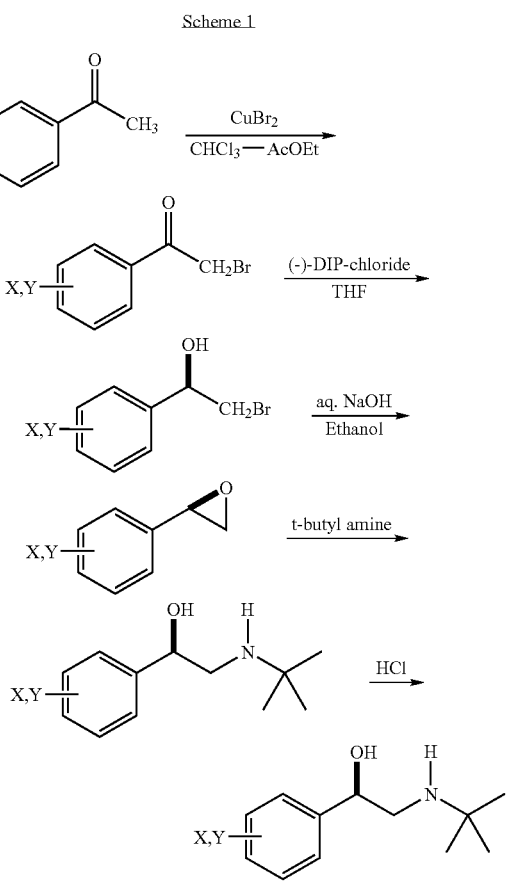

Scheme 1

In this scheme, the key asymmetric reduction reagents are B-chlorodiisopinocampheyl-boranes (DIP-Chloride™): (−)-DIP-chloride™ is used for preparation of "R" alcohol, and (+)-DIP-chloride ™ for preparation of "S" alcohol. These reagents have been developed for the general preparation of chiral alcohols. (For reviews on the chemistry of DIP-chloride™ see: Brown et al. Acc. Chem. Res. 1992, 25, 16; Brown and Ramachandran in Advances in Asymmetric Synthesis, Vol 1, Hassner, A., Ed., JAI Press: Greenwich, Conn., 1994, pp-144-20; Ramachandran and Brown, in Reductions in Organic Synthesis, Chap. 5, Abdel-Magid, A., Ed., American Chemical Society: Washington, D.C., 1996), and are available commercially or may be prepared in the laboratory by one skilled in the art.

The leaving group bromo is displaced by a primary amine resulting in the protected product. Depending on the requirements, protecting groups may be removed from substituents X Y and/or Z to provide the final 2-phenyl-2-ethanolamine in high enantiomeric purity, typically ≧98%.

The groups X, Y and Z are substituents that impart value to the 2-phenyl-2-ethanolamines, such as activity as β-adrenergic agonists or growth promoters in livestock. Examples of preferred substituents X and Y are hydroxyl, hydroxymethyl, amino, formamido, N,N-dimethylcarbamoyl and related groups. Examples of preferred substituent Z are tert-butyl, $(CH_2)_6O(CH_2)_4$—$C_6H_5$, $CH(CH_3)$—$C_6H_4$-4-$OCH_3$ and related groups.

Acid salts of the chiral 2-phenyl-2-ethanolamine products may also be prepared using the methods of this invention. Suitable salts include those derived from inorganic acids, such as sulfates and hydrochlorides, and those derived from organic acids, such as mesylates, fumarates, tartrates, citrates, maleates, succinates, and benzoates.

Uses of R-bambuterol

In clinical use R-bambuterol, the compound of the invention, will be administered orally, by injection or by inhalation, or may be absorbed via skin or rectum in the form of a pharmaceutical preparation comprising the compound of the invention as the active ingredient.

R-Bambuterol can be used:
(a) as a bronchospasmolytic agent in various asthmatic conditions.
(b) as a lipid lowering agent in hyperlipidemia or other related conditions
(c) to moblize excess fat tissue in animals or humans as a result of its plasma triglyceride lowering activity.
(d) for relaxing human uterus, gall bladder, bladder or blood vessels, organs and tissues which containing $β_2$ receptors.

EXAMPLES

Preparation of R-bambuterol

R-bambuterol hydrochloride is prepared by the method of this invention as illustrated in Scheme 2. All reagents were available commercially. NMR spectra were recorded on a Bruker Avance instrument at 300 Mz for $^1$H. Chiral HPLC was done on a Waters instrument [column: Chiralcel OJ; mobile phase: 91(hexanes)/10(ethanol)/0.1(diethylamine); UV detection: 220 nm].

Scheme 2

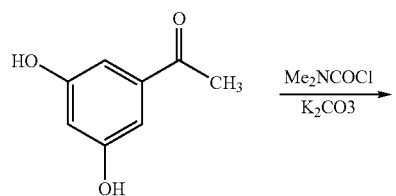

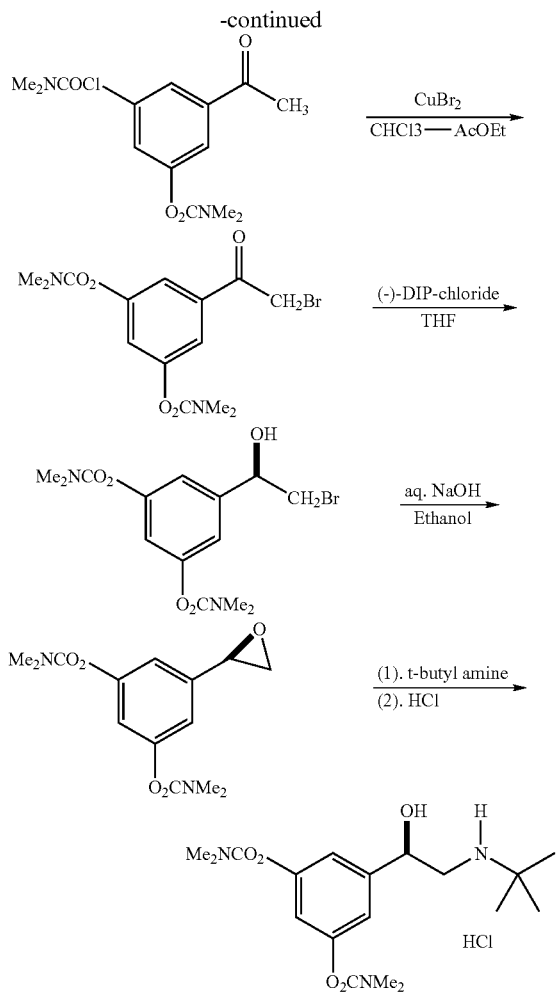

Step 1.
3,5-di(N,N-dimethylcarbamyloxy)acetophenone

A mixture of 3,5-dihydroxyacetophenone (24 g, 0.16 mole), dimethylcarbamyl chloride (50 g, 0.46 mole), potassium carbonate 1.5H$_2$O (41 g, 0.25 mole), anhydrous potassium carbonate (9.4 g, 0.07 mole) and pyridine (1 g) in ethyl acetate (150 mL) was stirred at 70° C. for 2 hours. Water (120 mL) was added to the mixture, and the resulting mixture was stirred at 70° C. for 1.5 hours. After cooling to room temperature, the reaction mixture was separated, and the organic phase was washed with dilute sulfuric acid (2%), dried over MgSO$_4$, filtered, and the filtrate was concentrated to give the product: 40 g, yield 86%. $^1$H NMR (CDCl$_3$) δ 2.58 (s, 3H, COCH$_3$), 2.90, 3.10 (s, 12H, 2xN(CH$_3$)$_2$), 7.20 (s, 1H, H4), 7.55 (s, 2H, H2,6).

Step 2. 2'-Bromo-3,5-di(N,N-dimethylcarbamyloxy) acetophenone

A mixture of 3,5-di(N,N-dimethylcarbamyloxy)acetophenone (38 g, 0.13 mole), copper (ED bromide (57.7 g, 0.26 mole) in ethyl acetate (100 mL) and chloroform (100 mL) was stirred at reflux for 5 hours. The mixture was filtered to remove the solid, and the filtrate was washed with water, dried over MgSO$_4$, and filtered. The filtrate was concentrated and the product crystallized: 44.1 g, yield 91%. $^1$H NMR (CDCl$_3$)

δ 3.04, 3.12 (s, 12H, 2xN(CH$_3$)$_2$), 4.40 (s, 2H, CH$_2$), 7.25 (s, 1H, H4), 7.58 (s, 2H, H2,6) ppm.

Step 3. (R)-1-Bromo-2-[3,5-bis(N,N-dimethylcarbamyloxy)phenyl)]-2-ethanol

A solution of 2'-bromo-3,5-di(N,N-dimethylcarbamyloxy)acetophenone (11 g, 30 mmole) in anhydrous tetrahydrofuran (100 mL) was added to a solution of (−)-DIP-Chloride (10.6 g, 33 mmole) in anhydrous tetrahydrofuran (60 mL) at −25° C. under nitrogen. The resulting solution was stirred at −25° C. for 60 hours, then warmed to 0° C., and diethanolamine (7 g, 66 mmole) was added dropwise. The mixture was warmed to room temperature and stirred for 2 hours, whereupon the boranes precipitated as a complex which was filtered and washed with pentane. The combined solvents were removed by distillation, and the residue was purified by silica gel column chromatography to give the product as an oil: 8.4 g, yield 75%. $^1$H NMR (CDCl$_3$), consistent.

Step 4. (S)-2-[3,5-di(N,N-dimethylcarbamyloxyl)phenyl]oxirane.

A 15% solution of NaOH in water (100 mL) was added to a solution of (R)-1-bromo-2-[3,5-di(N,N-dimethylcarbamyloxy)phenyl)]-2-ethanol (7.0 g, 18.7 mmole) in ethanol (100 mL). The mixture was stirred at room temperature for 2 hours. The reaction mixture was concentrated, treated with water, extracted with ethyl acetate. The organic layer was washed with brine and water, and dried over MgSO$_4$. The filtrate was evaporated and the residue dried under vacuum to give the product: 5.5 g, yield 100%. The product was used in the next step without further purification. 1H NMR (CDCl3) δ 2.56, 3.15 (dd, 2H, CH2), 4.20 (dd, 1H, CH), 3.0, 3.10 (s, 12H, 2xN(CH3)2), 7.22 (s, 2H, H2,6), 7.56 (s, 1H, H4) ppm. Chiral HPLC, ee 98.7% (R, 99.35%, S, 0.65%).

Step 5. R-Bambuterol hydrochloride.

A mixture of (S)-2-[3,5-di(N,N-dimethylcarbamyloxy)phenyl]oxirane (5.5 g, 18.7 mmole) in t-butylamine (80 mL) was stirred at reflux for 3 days. The mixture was concentrated to dryness, treated with water, and extracted with ethyl acetate. The organic layer was washed with water and dried over MgSO$_4$. The filtrate was concentrated and the residue treated with a solution of hydrogen chloride in diethyl ether to give R-bambuterol hydrochloride as white solid: 5.2 g, yield, 69%. $^1$H and $^{13}$C NMR (D$_2$O) 1.30 (s, 9H, (CH3)3), 2.90, 3.06 (s, 12H, 2xN(CH3)2), 3.10, 3.25 (dd, 2H, H2',2"), 4.95 (dd, 1H, H1'), 6.88 (s, 1H, H4), 7.06 (s, 2H, H2,6) ppm. Chiral HPLC, ee 99.4% (R, 99.7%, S, 0.3%).

Pharmacologic Tests of R-bambuterol Hydrochloride

A. Effects on Bronchospasm

A1. Protection Against Histamine-Evoked Asthma in Conscious Guinea Pigs.

Test methods: Guinea pigs (Dunki-Hartley strain, 190±30 g) were fasted overnight but given water ad libidum. The animals were restrained individually in a glass chamber and exposed to aerosol histamine generated by a nebulizer from a 0.2% aqueous solution of histamine under constant pressure at dose of 0.5 ml/min for a period of 15 sec. The animal was removed from the chamber, and its behavior was monitored. A sign of collapse and the latency time from exposure to collapse were recorded. Only the animals with latency time less than 120 sec, as an indication of sensitive to histamine, were chosen for later experiments. The animals chosen were allowed to recover completly by resting for 24 hours before experiments. Test compounds and racemic bambuterol hydrochloride were dissolved in saline.

Time course of the effect of test compounds: R-Bambuterol hydrochloride or racemic bambuterol hydrochloride at 2, 4 and 8 mg/kg, and vehicle alone, were administered to the guinea pigs orally via a stomach tube. Exposure of treated animals to aerosol histamine (as above) was done at 1, 4 and 24 hours after treatment. For each experimental group, there were a total of 8 animals with equal number of both sexes, and no repeated exposure was made for individual experimental animals.

Study of dose-response of test compounds: Four hours before the exposure to aerosol histamine, animals were randomized into groups (n=8, equal male and female), and given R-bambuterol hydrochloride or racemic bambuterol in doses of 0.25, 0.5, 1.0, 2.0, 4.0 and 8.0 mg/kg, and vehicle control, orally via a stomach tube. The numbers of collapsed animal as a result of asthmatic reaction to aerosol histamine were counted, and the latency times were recorded. Both of these parameters were used as quantitative measurements of the protective effects of the treatments on bronchospasm evoked by aerosol histamine. For animals showing no sign of severe asthma and which did not collapse over period of 360 sec, it counted as no collapse and the latency time was recorded as 360 sec.

Test results: Results are summarized in Tables 1 to 3. As shown in Table 1, oral administration of R-bambuterol and racemic bambuterol at doses of 2 to 8 mg/kg has significant protective effects on asthma evoked by exposure to aerosol histamine in guinea pigs. The effects were shown within one hour of administration and lasted for 24 hours. The maximum protective effects were seen 4 hours after administration. After 1 and 4 hours of administration, R-bambuterol at 2 and 4 mg/kg had stronger protecting effect than racemic bambuterol at the same doses (P<0.01). This indicates that R-bambuterol was about twice as potent as racemic bambuterol.

TABLE 1

Effects of oral administration of R-bambuterol or racemic RS-bambuterol on response to aerosol histamine exposure in conscious guinea-pigs.

|  | 1st Hour | | 4th Hour | | 24th Hour | |
| --- | --- | --- | --- | --- | --- | --- |
|  | Collapsed | Latency | Collapsed | Latency | Collapsed | Latency |
|  | n    % | sec | n    % | sec | n    % | sec |
| Control # R-bambuterol | 8.0  100 | 47 ± 16 | 8.0  100 | 43 ± 13 | 8.0  100 |  |
| 2 mg/kg | 4.0  50.0* | 231 ± 70 | 2.0  25.0* | 295 ± 65 | 5.0  62.5 | 202 ± 67 |

TABLE 1-continued

Effects of oral administration of R-bambuterol or racemic RS-bambuterol on response to aerosol histamine exposure in conscious guinea-pigs.

|  | 1st Hour | | | 4th Hour | | | 24th Hour | | |
| --- | --- | --- | --- | --- | --- | --- | --- | --- | --- |
|  | Collapsed | | Latency | Collapsed | | Latency | Collapsed | | Latency |
|  | n | % | sec | n | % | sec | n | % | sec |
| 4 mg/kg | 3.0 | 37.5* | 258 ± 71 | 0.0 | 0.0* | >360 | 4.0 | 50.0 | 242 ± 64 |
| 8 mg/kg | 2.0 | 25.0 | 299 ± 57 | 0.0 | 0.0 | >360 | 3.0 | 37.5 | 256 ± 72 |
| RS-bambuterol | | | | | | | | | |
| 2 mg/kg | 6.0 | 75.0 | 168 ± 61 | 4.0 | 50.0 | 227 ± 56 | 5.0 | 50.0 | 208 ± 65 |
| 4 mg/kg | 5.0 | 62.5 | 199 ± 63 | 2.0 | 25.0 | 299 ± 51 | 3.0 | 37.5 | 287 ± 57 |
| 8 mg/kg | 3.0 | 37.5 | 260 ± 66 | 0.0 | 0.0 | >360 | 2.0 | 25.0 | 303 ± 54 |

\# Significant difference compared to all other groups (P < 0.01)
*Significant difference in comparison with racemic bambuterol (P < 0.05)

Table 2 shows the protective effect of orally administered R-bambuterol at different dosages on exposure of conscious guinea pigs to aerosol histamine in comparison with the effect of racemic bambuterol. In both cases, the effect was dose-dependent. Full protective effect was seen at 4 mg/kg of R-bambuterol, whereas fall protection by racemic bambuterol required 8 mg/kg. The $ED_{50}$ for R-bambuterol and racemic bambuterol were 0.91 mg/kg and 1.68 mg/kg, respectively.

TABLE 2

Comparison of the effects of R-bambuterol and racemic bambuterol on collapse of guinea pigs exposed to aerosol histamine.

| Dose (mg/kg) | 0 | 0.25 | 0.5 | 1 | 2 | 4 | 8 |
| --- | --- | --- | --- | --- | --- | --- | --- |
| No. of animals | n = 8 | n = 8 | n = 8 | n = 8 | n = 8 | n = 8 | n = 8 |
| % collapse, R-bambuterol | 100 | 87.5 | 75 | 50 | 25 | 0 | 0 |
| % collapse, RS-bambuterol | 100 | 100 | 87.5 | 75 | 50 | 25 | 0 |

Table 3 shows the effects on latency of orally administered R-bambuterol compound at difference doses on guinea pigs exposed to aerosol histamine in comparison with the effects of racemic bambuterol. The protective effect is indicated as an increase in latency time to collapse after exposure to aerosol histamine. The effect in both cases was dose-dependent. The effect of 2 mg/kg of R-bambuterol was equivalent to that of 4 mg/kg of racemic bambuterol. The maximum effects were seen at 4 mg/kg of R-bambuterol and 8 mg/kg of racemic bambuterol.

TABLE 3

Comparison of the effects of R-bambuterol and racemic-bambuterol on latency time of collapse in animals exposed to aerosol histamine

| Dose (mg/kg) | 0 | 0.25 | 0.5 | 1 | 2 | 4 | 8 |
| --- | --- | --- | --- | --- | --- | --- | --- |
| No. of animals | n = 8 | n = 8 | N = 8 | n = 8 | n = 8 | n = 8 | n = 8 |
| Latency (sec), R-bambuterol | 43 | 110 | 160 | 209 | 295 | >360 | >360 |
| Latency (sec), RS-bambuterol | 44 | 61 | 114 | 151 | 227 | 299 | >360 |

A2. Protection Against Allergic Bronchospasm in Sensitized Conscious Guinea Pigs Test method: Guinea pigs (Dunkin-Hartley strain, 200±10 g, equal sexes) were used in this study. Ovalbumin (5%) solution was injected into guinea pigs subcutaneously and intraperitoneally to sensitize the animals. Male and female sensitized animals were kept separately for 14 days, and food and water was available ad libitum. On day 14 after sensitization, animals were randomized into groups of 8 each. The animals were treated orally with saline (control) or various concentrations of R-bambuterol or racemic bambuterol in saline. Four hours after the treatment, each animal was restrained in a glass chamber. After stabilization the animal was exposed to an aerosol of ovalbumin generated by a nebulizer from a 5% solution of ovalbumine at a rate of 0.5 ml/min for a period of 15 seconds. The animal was removed from the chamber, and the behavior of the animal was monitored. The number of the sensitized animals which collapsed were counted, and the latency time, i.e. the time from the exposure to aerosol ovalbumin to the collapse of the animal, was recorded. Animal that did not show signs of severe asthma and did not collapse over a period of 360 seconds were copunted as no collapse and the latency time was recorded as 360 seconds.

Test results: Results are summarized in Table 4. Exposure of ovalbumin-sensitized guinea pigs to aerosols of antigen evoked severe asthmatic reaction in the control group. All 8 animals tested collapsed with a latency of 58±9 sec. However, in the group treated with 8 mg/kg of R-bambuterol, none of the 8 animals collapsed within the 360 second observation period. At the same dose of racemic bambuterol, 2 of 8 animals collapsed with latency of 316±36 seconds. The protective effect of 4 mg/kg of R-bambuterol was similar to that of 8 mg/kg of racemic bambuterol. The number of collapsed animals were less and the latency time from the exposure to collapse are significantly longer in the groups treated with 4 mg/kg or 8 mg/kg of R-bambuterol compared with the groups treated with the same doses of racemic bambuterol. These results indicate that R-bambuterol is more potent than racemic bambuterol in protecting guinea pigs from allergic bronchospasm.

TABLE 4

Protective effect of R-bambuterol against allergic bronchospasm of sensitized guinea pigs in comparison with racemic bambuterol.

| Treatment | Number collapsed | % collapsed | Latency time (sec) |
| --- | --- | --- | --- |
| Control (n = 8) | 8 | 100 | 58 ± 9 |
| R-bambuterol: | | | |
| 1 mg/kg (n = 8) | 5 | 63 | 193 ± 30* |
| 4 mg/kg (n = 8) | 2 | 25 | 293 ± 27*# |

TABLE 4-continued

Protective effect of R-bambuterol against allergic bronchospasm of sensitized guinea pigs in comparison with racemic bambuterol.

| Treatment | Number collapsed | % collapsed | Latency time (sec) |
|---|---|---|---|
| 8 mg/kg (n = 8) | 0 | 0 | >360*# |
| Racemic bambuterol: | | | |
| 1 mg/kg (n = 8) | 6 | 75 | 156 ± 38* |
| 4 mg/kg (n = 8) | 3 | 38 | 174 ± 21* |
| 8 mg/kg (n = 8) | 2 | 25 | 316 ± 36* |

*Significant difference compared to control (P < 0.01)
Significant difference ompared to racemic bambuterol A3. Bronchodilating Effects of the Test Compound on Isolated Guinea Pig Lung Strip.

Test method: Guinea pigs (Dunlin-Hartley, ca. 400 g) were used. After anesthesia, the chest was opened and sections of lung tissue about 3 mm in width, were dissected quickly from a lower lobe with the longitudinal axis of the strip cut parallel to the bronchus. The strips were further divided into two thin strips with approximate dimension of 20×3×3 mm. With threads attached to each end, strips were mounted in organ baths containing aerated Krebs solution at 37° C. A load of between 0.5-1.0 g force was applied by gentle stretching, and the tissue was allowed to equilibrate for 60 min with the solution changed at 20 min intervals. The lung strips were pre-contracted by $10^{-5}$ M histamine, then an equal volume of solution containing R-bambuterol or racemic bambuterol was added cumulatively into the organ bath. The contractions of the lung strips were measured isometrically with force-displacement transducers and recorded.

Preparation of solutions of test compounds: Both R-bambuterol and racemic bambuterol hydrochlorides are inactive pro-drugs, which are hydrolyzed into the parent drugs, R-terbutaline and racemic terbutaline, respectively, mainly by plasma cholinesterase. Based on the pharmacokinetic studies of racemic bambuterol hydrochloride, about 50% of absorbed bambuterol is hydrolyzed to terbutaline, the active-parent form, in plasma. There is little cholinesterase in the lung strip preparation, so neither the test compound nor racemic bambuterol has significant effects. In order to test the compound of invention in vitro on isolated guinea-pig lung tissue, R-bambuterol and racemic bambuterol were administrated orally to guinea pigs at a dose of 8 mg/kg. Four hours later, blood was collected from the animals, and the serum containing the active parent form of the test compounds were prepared. The concentration of the active parent form, i.e. terbutaline, in serum measured using BPLC, was 64-70 ng/ml in the animal treated with R-bambuterol and 62-69 ng/ml in the animal treated with racemic bambuterol. The serum containing the active form of test compound was then added into the organ in a certain volume, so that the final concentration of the active forms of test compounds was 0.25 ng/ml in the organ bath. Concentration-response relationships were obtained using a cumulative dose schedule by adding the same volume of the serum into the organ bath. The test using the serum containing the active form of racemic bambuterol was done in parallel with the test compound in the same manner as described above.

Test results: It can be seen in Table 5 that the active form of R-bambuterol had a significantly greater relaxation effect on lung strip contractions than the active form of racemic bambuterol.

TABLE 5

Effect of serum containing the active forms of R-bambuterol and racemic bambuterol on contractions of isolated guinea-pigs lung strips.

| | Percent of Relaxation | |
|---|---|---|
| Conc. (ng/ml) | Active form* of R-bambuterol n = 4 | Active form of RS-bambuterol n = 4 |
| 0.25 | 12.4 ± 1.3 | 7.6 ± 0.8 |
| 0.50 | 19.5 ± 2.2 | 10.8 ± 2.1 |
| 0.75 | 43.7 ± 1.8 | 26.5 ± 3.4 |
| 1.00 | 60.1 ± 5.7 | 39.6 ± 4.0 |
| 1.25 | 75.6 ± 8.4 | 45.7 ± 6.7 |

*All values in group treated with serum containing the active form of R-bambuterol were significantly different compared with the group treated with serum containing the active form of racemic bambuterol (P < 0.01).

B The Lipid Lowering Effects of R-bambuterol

Test method: Male and 35 female mice, Kunming strain, 35 each, weight 18-22 grams, were used. Food and water were available ad libitum. The animals were randomized into 7 groups (n=10). Groups of animals were administered orafly, via a stomach tube, vehicle (distilled water, two groups), R-bambuterol hydrochloride (10 mg/kg and 5 mg/kg), racemic bambuterol hydrochloride (10 mg/kg and 5 mg/kg) and simvastatin (10 mg/kg) once a day for four days. With the exception of one vehicle—treated group (as control), Tyloxapol (400 mg/kg, Sigma Chemical Co.) was injected into the peritoneal cavity of the mice of all groups immediately after the last treatment on the fourth day in order to induce hyperlipidemia. All the animals were fasted overnight prior to the injection of Tyloxapol. Blood samples were collected by cardiac puncture 24 hours after the injection of Tyloxapol. The blood samples were processed to plasma, and concentration of triglycerides (TG), cholesterol (CHO), high density lipoprotein (HDL), low density lipoprotein (LDL) and very low density lipoprotein (VLDL) were measured with an autoblood analyzer (Olympic, Japan).

Test result: Administration of Tyloxapol to a vehicle-treated group resulted in significant increases in TG, CHO, LDL and VLDL, but not HDL, relative to the control, vehicle treated group without Tyloxapol (Table 6). However, there was significantly less or even no increases in TG, CHO, LDL and VLDL in the groups pre-treated with R-bambuterol, racemic bambuterol and simvastatin. These results are summarized in Table 6.

TABLE 6

Lipid lowering effects of test compound in hyperlipidemia mice

| | Lipid levels (mg/dl) | | | | |
|---|---|---|---|---|---|
| | TG | CHO | VLDL | LDL | HDL |
| Control* | 154 ± 25 | 104 ± 18 | 35 ± 6 | 20 ± 5 | 49 ± 8 |
| Tyloxapol# | 816 ± 115 | 240 ± 83 | 111 ± 54 | 54 ± 23 | 63 ± 20 |

TABLE 6-continued

Lipid lowering effects of test compound in hyperlipidemia mice

| | Lipid levels (mg/dl) | | | | |
|---|---|---|---|---|---|
| | TG | CHO | VLDL | LDL | HDL |
| Tyl + R-bambuterol 5 mg* | 323 ± 176 | 189 ± 83 | 50 ± 26 | 34 ± 15 | 42 ± 27 |
| Tyl + R-bambuterol 10 mg* | 105 ± 18# | 119 ± 16 | 35 ± 7 | 29 ± 5 | 53.3 ± 6.7 |
| Tyl + bambuterol 10 mg* | 148 ± 45 | 125.2 ± 19.8 | 44.2 ± 14.4 | 30 ± 6 | 50 ± 17 |
| Tyl + simvastatin 10 mg@ | 311 ± 187* | 176 ± 64 | 85 ± 50 | 42 ± 11 | 49 ± 16 |

Tyl. Tyloxapol
*Significant difference, in comparison with the values in the Tyloxapol group, in the levels of TG, CHO, VLDL and LDL, but not HDL. In Tyl + simvastatin group only the value of TG was found significantly different from that in the Tyloxapol group.
Significant difference between the values in Tyl + R-bambuterol 10 mg and control groups
@Significant difference in comparison with the values in Tyl + R-bambuterol 10 mg group.
No significant differences were found in HDL among all groups.

The results in Table 6 indicate that R-bambuterolo at both 5 mg/kg and 10 mg/kg significantly lowered triglycerides, cholesterol, VLDL and LDL in hyperlipidemic mice. At 10 mg/kg, R-bambuterol showed larger lowering effects than at 5 mg/kg, although only the differences in TG were significant ($p<0.01$). At 10 mg/kg, R-bambuterol lowered values in hyperlipidemic mice to the values similar to those in the control, non-hyperlipidemic group. R-bambuterol has significantly larger lowering effects on TG, CHO, VLDL and LDL in comparison with the same dose of simvastatin (10 mg/kg). The values in the hyperlipidemic groups treated with R-bambuterol (10 mg/kg) or bambuterol (10 mg/kg) were similar to thosein control, non-hyperlipidemic mice. However, there is a further reduction in plasma triglycerides in hyperlipidemic mice treated with 10 mg/kg of R-bambuterol. The triglycerides in this group were significantly less than in the control, non-hyperlipidemic group. The same effect was not seen in the mice treated with either 10 mg/kg bambuterol or 10 mg/kg simvastatin.

C. Cardiovascular Effects of R-bambuterol in Rats.

Test method: Rats (Sprague Dawley, 250-300 g) were were randomized into two groups (n=6, equal sexes). After anesthesia, plastic tubing was introduced into a carotid artery of each animal and connected to pressure transducers to record mean artery pressure (MBP) and heart rate (HR). Another tube was introduced into the left ventricular chamber via the another carotid artery and connected to a pressure transducer. Left ventricular systolic pressure (LVSP) and the first order of differential of LVSP (dp/dt) as an index for inotropic effects were recorded. R-Bambuterol and racemic bambuterol hydrochloride were dissolved in saline and administrated intravenously at 30 mg/kg to each animal. The HR, MBP and Max dp/dt were measured before treatment (control) and after the treatments when the maximum response occurred, and 20 min after treatment as indication of recovery.

Test result: The results of these experiments are summarized in table 7. R-Bambuterol showed some degree of chronotropic effects as indicated by increase in HR and a mild inotropic effects as indicated by the increase of Max dp/dt at the dose of 30 mg/kg. These effects are not significant compared with racemic bambuterol hydrochloride of the same dose. However, the increase is significantly less in Max dp/dt in the rats treated with R-bambuterol (12.9% of control) than with racemic bambuterol (24.4% of control). This indicates that the test compound has less inotropic effects on the heart than racemic bambuterol at the dose given. During the recovery period (20 min after treatment), the HR returned toward control (3.7% of control) in animals treated with R-bambuterol, but the same value was significantly higher (9.5%) in animals treated with racemic bambuterol hydrochloride. This indicates that the chronotropic effect of R-bambuterol is significantly shorter in duration compared with racemic bambuterol.

TABLE 7

Cardiovascular effects of R-bambuterol and bambuterol, 30 mg/kg, in rats.

| | HR (Beat/min) | % of Control | MBP (Kpa) | % of control | Maxdp/dt (Kpa/sec) | % of control |
|---|---|---|---|---|---|---|
| R-Bambuterol: | | | | | | |
| Control | 402 ± 38 | | 14.1 ± 1.7 | | 297 ± 84 | |
| Treatment Δ | 95 ± 12 | 23.6% | 4.9 ± 0.8 | 34.8% | 38.4 ± 3.5* | 12.9% |
| 20 min afterΔ | 15 ± 9* | 3.7% | 1.3 ± 0.6 | 9.8% | 14.8 ± 3 | 5.0% |
| Rac-Bambuterol: | | | | | | |
| Control | 412 ± 67 | | 13.3 ± 1 | | 268 ± 71 | |
| Treatment Δ | 85.8 ± 5 | 20.6% | 4.2 ± 0.5 | 31.6% | 65.4 ± 9* | 24.4% |
| 20 min afterΔ | 40 ± 9* | 9.5% | 1.1 ± 0.4 | 8.3% | 13 ± 3.8 | 4.8% |

HR, heart rate.
MBP, mean blood pressure.
Max dp/dt, maximum value of first order differential of left ventricular systolic pressure.
*significant difference in comparison with the same values in the bambuterol group respectively ($p < 0.01$)

Comments on the results of pharmacological tests of R-bambuterol.

R-Bambuterol:

1. is a potent bronchodilator and oral administration produces a long lasting protection of animals from asthmatic reaction to spasmogen or antigen. R-Bambuterol is about twice as potent as racemic bambuterol in this effect.

2. given orally, can either prevent the collapse or increase the latency time of collapse of conscious guinea pigs exposed to aerosol histamine. R-Bambuterol is twice as potent as racemic bambuterol in this effect.

3. given orally at 4 mg/kg, can prevent collapse in animals exposed to aerosol histamine, an effect requiring 8 mg/kg of racemic bambuterol. These protecting effects of R-bambuterol last over 24 hours after oral administration.

3has potent lipid-lowering effects in hyperlipideniic animals, an effect which can restore the plasma triglycerides, cholesterol, VLDL and LDL the level of normal control animals. R-Bambuterol has significantly stronger effects on lowering plasma triglycerides than racemic bambuterol and simvastatin in hyperlipidemic animals.

4has less chronotropic and inotropic side effects than the same dose of racemic bambuterol in rats.

In summary, R-bambuterol offers a good alternative in treating asthma with a better benefit/risk ratio than racemic bambuterol. It is a more potent bronchospasmolytic agent with less cardiac side effects than racemic bambuterol. It is also a potent lipid-lowering agent, particularly in treating hypertriglyceridemia.

We claim:

1. A method for the treatment of asthma or a reversible obstructive airway or lung ailment in animals or in human, comprising administering a therapeutically effective amount of an optically pure R isomer of bambuterol or pharmaceutically acceptable salt thereof while reducing toxicity associated with bambuterol, said R isomer of bambuterol is in at least 80% enantiomeric excess.

2. The method of claim 1 wherein the administering is by oral, intravenous, or subcutaneous route or by absorbing through skin or rectum.

3. A method for treating hyperlipidemia or hyperglyceridemia in animals or in human, comprising administering a therapeutically effective amount of an optically pure R isomer of bambuterol or pharmaceutically acceptable salt thereof while reducing toxicity associated with bambuterol, the said R isomer of bambuterol is in at least 80% enantiomeric excess.

4. The method of claim 3 wherein the administering is by oral, intravenous, or subcutaneous route or by absorbing through skin or rectum.

5. The method according to claim 1, wherein the R isomer of bambuterol is in at least 98% enantiomeric excess.

6. The method according to claim 3, wherein the R isomer of bambuterol is in at least 98% enantiomeric excess.

* * * * *